United States Patent [19]

Poli et al.

[11] Patent Number: 5,212,160

[45] Date of Patent: * May 18, 1993

[54] 3-L-(5-THIOXO-L-PROLYL)THIAZOLIDINE-4-CARBOXYLIC ACID AND DERIVATIVES THEREFROM, PROCESSES FOR THE PREPARATION THEREOF AND PHARMACEUTICAL COMPOSITIONS CONTAINING THEM

[75] Inventors: Stefano Poli; Lucio Del Corona; Germano Coppi, all of Milan, Italy

[73] Assignee: Poli Industria Chimica S.p.A., Milan, Italy

[*] Notice: The portion of the term of this patent subsequent to Nov. 19, 2008 has been disclaimed.

[21] Appl. No.: 652,792

[22] Filed: Jan. 16, 1991

[30] Foreign Application Priority Data

Jan. 23, 1990 [IT] Italy .............................. 19133 A/90

[51] Int. Cl.$^5$ .......................... C07K 5/06; A61K 37/02
[52] U.S. Cl. .......................................... 514/19; 548/201
[58] Field of Search .......................... 548/201; 514/19

[56] References Cited

U.S. PATENT DOCUMENTS

| | | | |
|---|---|---|---|
| 4,839,387 | 6/1989 | Poli | 514/19 |
| 5,066,644 | 11/1991 | Poli | 514/19 |

OTHER PUBLICATIONS

Andersen Liebigs Ann Chem. 1987 59.
Andersen, Liebigs Ann Chem 1986 269.
1–Pharmacology 13, 98, 1983, 154921m.
1–Pharmacology 47, 103, 1985, 171723n.
Scotini et al; Pharmacol. Res. Commun. 131, 15, 1983.
Fassina et al; Naunyn–Schiedeberg's Arch. Pharmacol. 222, 330, 1985.
2–Mammalian Hormones 104, 1986 162227x.
2–Mammalian Hormones 87, 104, 1986, 62252h.

*Primary Examiner*—Robert Gerstl
*Attorney, Agent, or Firm*—Walter H. Schneider

[57] ABSTRACT

3-L-(5-thioxo-L-prolyl)thiazolidine-4-carboxylic acid and the derivatives thereof have valuable immunostimulating, antioxidant, antiradical and antiageing properties. They are prepared by thionating the corresponding 3-L-pyroglutamyl-L-thiazolidine-4-carboxylic acid derivatives or by condensing 5-thioxo-L-proline with the corresponding L-thiazolidine-4-carboxylic acid derivatives.

6 Claims, No Drawings

3-L-(5-THIOXO-L-PROLYL)THIAZOLIDINE-4-CARBOXYLIC ACID AND DERIVATIVES THEREFROM, PROCESSES FOR THE PREPARATION THEREOF AND PHARMACEUTICAL COMPOSITIONS CONTAINING THEM

The present invention relates to the compounds of general formula (I)

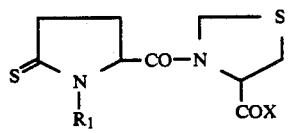

wherein $R_1$ is hydrogen, $C_1$-$C_8$ alkyl, $C_6$-$C_8$ aryl and aralkyl, $C_2$-$C_{10}$ acyl, $C_2$-$C_{10}$ straight or branched alkoxyalkyl containing 1-3 oxygen atoms, $C_3$-$C_8$ alkylcarbonylalkyl, and X is —OH, $C_1$-$C_8$ alkoxy, aralkoxy or dialkylamino-$C_1$-$C_{10}$-alkoxy, an amino group, the residue from an aliphatic primary or secondary $C_1$-$C_8$ amine optionally containing one or more double and/or triple bonds, the residue from a primary aralkylamine or from a cyclic aliphatic $C_4$-$C_8$ amine optionally interrupted by an oxygen atom, and to the pharmaceutically acceptable salts thereof.

In the compounds of formula (I), $R_1$ is preferably hydrogen $C_1$-$C_4$ alkyl, phenyl, benzyl, acetyl, methoxyethyl, methoxy- or ethoxy-carbonyl-methyl or -ethyl. More preferably, $R_1$ is hydrogen, methyl or ethyl. X is preferably hydroxy, methoxy, ethoxy, phenoxy, benzyloxy or an amino, ethylamino, allylamino, propargylamino, cyclopropylamino, pyrrolidino, piperidino, morpholino, diethylamino group.

The compounds of the invention can be prepared according to the reaction scheme A below, by reacting 3-L-pyroglutamyl-L-thiazolidine-4-carboxylic acid (II) (X=OH) or the esters or amides thereof (see Italian patent application no 19165/A/87) with a thionating agent, such as the Lawesson's reagent, in aprotic solvents such as dimethoxyethane, benzene, toluene or tetrahydrofuran.

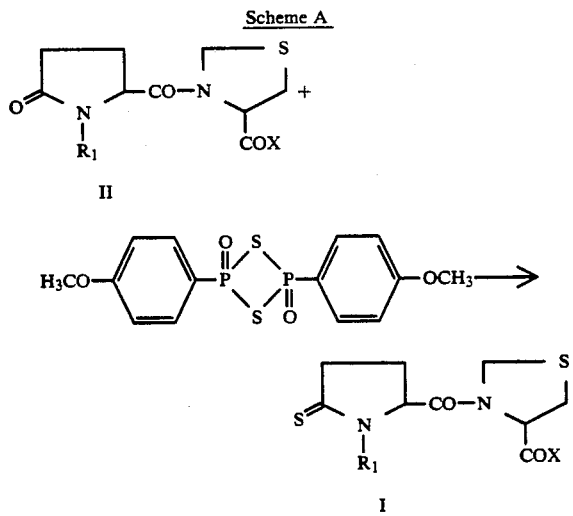

In the above scheme, $R_1$ and X are as above defined. The compounds (II) in which X is different from hydroxy can be prepared according to standard esterification or amidation techniques, starting from the free acid. Alternatively, compounds (I) can be prepared according to scheme B below:

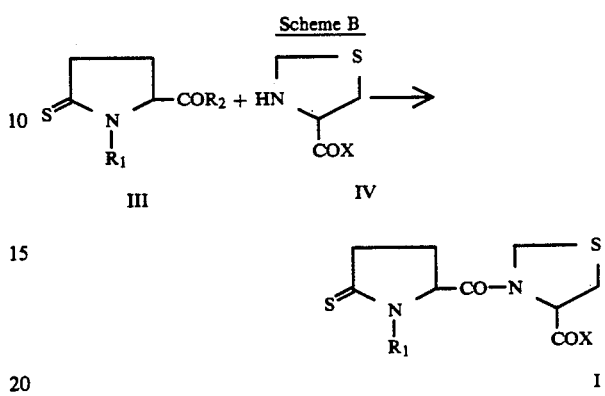

by reacting a 5-thioxoproline (III) reactive derivative, wherein $R_2$ can be pentachlorophenoxy, trichlorophenoxy, succinimidoxy, phthalimidoxy, imidazol-1-yl, and other groups generally used to activate the carboxy group, and $R_1$ has the above mentioned meanings, with a thiazolidine-4-carboxylic acid derivative (IV), wherein X has the above mentioned meanings, in aprotic solvents such as dimethylformamide, dimethoxyethane, tetrahydrofuran, dioxane and the like, optionally in the presence of tertiary bases such as triethylamine or tetramethylguanidine.

Compounds (III) and (IV) are known, or they can be prepared by conventional methods, starting from 5-thioxoproline and 4-thiazolidine-carboxylic acid, respectively.

The compounds of the invention have valuable pharmacological properties as well as very low acute toxicity.

More specifically, the compounds of the invention have interesting immuno-stimulating, antitoxic, antiradical and antiageing activities.

Since the production of the superoxide anion ($O_2$.) plays an important role in macrophage antimicrobial activity (N. P. Cumming, M. J. Pabst, J. Exp. Med., 152, 1659, 1980), the test for stimulation of the superoxide anion production in macrophages by medicaments is very important in the evaluation of the immuno-stimulating activity. Therefore, $O_2$. production in isolated peritoneal macrophages from prednisolone-immunodepressed animals treated with the compounds of the invention was evaluated. Mice were treated subcutaneously for 11 days with 0.5 mg/kg/day with prednisolone and with the tested compounds at a dose of 100 mg/kg intraperitoneally twice a day, whereas the day of killing they received the only compounds of the invention. Then macrophages were isolated by means of peritoneal washing and cultured in RPMI-1640 added with 10% bovine foetal serum at a concentration of $1 \times 10^6$ cells/ml and at a temperature of $+37°$ C. 1 ml aliquots of the cell suspension were incubated for 15 min. at 37° C. with cytochrome C from horse hearth and stimulated with phorbol myristate acetate (H. Nielsen, Eur. J. Clin. Pharmacol., 30, 99, 1986). After that, a spectrophotometric determination of reduced fer-ricytochrome C at $\lambda = 550$ nm was carried out, using an extinction coefficient E (550)=29.5 mM.

As shown in Table I, treatment with prednisolone induces an immunodepression which is evidenced by a lower production of the superoxide anion; simultaneous treatment with the compounds of the invention stimultes macrophages to produce $O_2$. in amounts near to those of not immunodepressed animals. Particularly, compounds Ia and Ib show higher activities than that of PGT (3-L-pyroglutamyl-L-thiazolidine-4-carboxylic acid, see Italian patent n. 1,202,426) the other compounds of the invention having a comparable activity, at the same weight dosage.

TABLE 1

Activity on superoxide anion production by prednisolone-immunodepressed murine peritoneal macrophages

| Treatment | Tests No. | Reduced cytochrome C nmoles/ $1 \times 10^6$ macrophages (mean ± s.e.) |
|---|---|---|
| 0.9% Nacl i.p. | 5 | 10.80 ± 0.66 |
| 0.9% NaCl i.p. + prednisolone 0.5 mg/kg/die/s.c. | 5 | 1.58 ± 0.58 |
| PGT 200 mg/kg/die i.p. + prednisolone 0.5 mg/kg/die/s.c. | 4 | 8.33 ± 0.77** |
| Ia 200 mg/kg/die i.p. + prednisolone 0.5 mg/kg/die/s.c. | 4 | 9.15 ± 0.68** |
| Ib 200 mg/kg/die i.p. + prednisolone 0.5 mg/kg/die/s.c. | 4 | 9.17 ± 0.68** |

**p <0.01 Dunnett's "t" test vs. immunodepressed control group

The antitoxic activity was tested by determining the capability of the compounds of the invention to protect rats against formaldehyde and acetaldehyde toxicities (Sprince et al., Agents and Actions, 9, 407, 1979). COBS CD(SD) Rats (C. River) weighing 180–200 g fasted since the night before were orally administered with the test compounds half an hour before and 5 hours after the oral administration of the toxic agent. Formaldehyde was administered at the dose of 900 mg/kg per os and acetaldehyde at the dose of 2150 mg/kg per os; mortality was controlled up to 72 hours later. The groups treated with the only toxic agents showed a mortality of 90–100%; compounds Ia and Ib gave an effective protection at the dose of 0.5 mM/kg (2 administrations), which protection being 60 and 70% against formaldehyde and 70 and 60% against acetaldehyde. The activity of the compounds of the invention is similar to that of ascorbic acid and L-cysteine. Since acetaldehyde and formaldehyde are an important portion of the toxic agents contained in cigarette smoke, these novel compounds are very important in the treatment of all the lung pathologies connected to tobacco abuse or to atmosphere pollution. The antiradical activity was tested against doxorubicin mortality in the mouse (R. D. Olson et al., Life Sci., 29, 1393, 1981). Groups of 10 male CD-1 mice (C. River) weighing 18–20 g were treated orally with the tested compounds; one hour later doxorubicin was administered at the dose of 22 mg/kg i.p. (10 ml/kg). Treatment was repeated with the tested compounds 6 hours after doxorubicin administration as well as the day after, with the same frequency (twice a day with a 7 hours interval between one treatment and the subsequent one). Mortality of the animals was checked for 14 days.

The doxorubicin treated group showed an 80–90% mortality; compounds Ia and Ib, at the dose of 0.5 mM/kg per os 4 times in two days give a protection against mortality of 40 and 50%, similar to that obtained with equal doses of L-cysteine and N-acetylcysteine.

The compounds of the invention are also active against paracetamol intoxication in the rat, at dosages superimposable to those of PGT. Moreover they have a radio-protective activity against ionizing radiations similar to that of PGT.

The compounds of the invention also improve neurocerebral performances and sexual behaviour in the elderly rat, with a reduction in the latencies and an increase in the coupling frequency.

Finally, compounds (I) can be used to counteract the excesses of oxidative processes, such as those deriving from chronic inflammatory processes or exposure to ionizing radiations.

The acute toxicities of compounds (I) in mice and rats by the oral and intraperitoneal routes, are higher than 3,000 mg/kg, which is very low, analogously to PGT.

The above data evidence that compounds (I) can be used in therapy for the treatment of a number of pathological conditions, such as immunodeficiencies, autoimmuno diseases, bronchopulmonary pathologies, as radical scavengers, and ageing processes.

The present invention also relates to pharmaceutical compositions suitably formulated for the oral administration, in form of soft or hard gelatin capsules, dragees, tablets, sachets, drops, syrups, sustained-release forms; and for the parenteral administration, in form of lyophilized vials and vials containing solutions of the active ingredients.

The pharmaceutical compositions of the present invention are prepared according to conventional techniques, using compatible pharmaceutically acceptable carriers and excipients and they also can contain, in combination, other active ingredients, having a complementary or anyhow useful activity.

The following non-limiting examples further illustrate the invention.

EXAMPLE 1

Ethyl 3-L-(L-5-thioxoprolyl)thiazolidine-4-carboxylate (I, $R_1$=H, X=OC$_2$H$_5$) (Ia).

A solution of 13.6 g (0.05 mole) of ethyl 3-L-pyroglutamyl-L-thiazolidine-4-carboxylate in 50 ml dimethoxyethane is added with 10.1 g (0.025 mole) of Lawesson's reagent and the mixture is stirred at room temperature for 45 min. The reaction mixture is filtered and added with an equal volume of ethyl ether. The solution is stirred for a while, then the product crystallizes, which is filtered and washed with dimethoxyethane-ether and dried. 11.3 g (57.6%) of the product are obtained, m.p. 111°–113° C.

For $C_{11}H_{16}N_2O_3S_2$ Calc. C %=45.83 H %=5.59 N %=9.73 S %=22.20 Found C %=45.68 H %=5.51 N %=9.58 S %=22.14 $[\alpha]_D^{20}$=−152.63° (C=1 CHCl$_3$)

$^1$H NMR (DMSO/TMS) δ=1.1 (t, 3H, CH$_3$); 1.7–2.6 (m, 4H, CH$_2$CH$_2$); 3–3.5 (s, 2H, SCH$_2$—C); 4–4.3 (m, 2H, CH$_2$CH$_3$); 4.35 (d, 1H, CHC$\overline{ON}$); 4.8–5 (m, 3H, N—$\overline{CH}_2$—S and $\underline{CH}$COO), 10.3 (s, 1H, N$\underline{H}$).

EXAMPLE 2

3-L-(5-thioxoprolyl)thiazolidine-4-carboxylic acid (I, $R_1$=H, X=OH) (Ib)

To a suspension of 4.32 g (0.015 mole) of the compound of Example 1 in 10 ml of water, 18 ml of N NaOH are added dropwise. The reaction mixture is stirred for 30 min. at room temperature and for 1.5 hours at 35°–40° C.; then it is cooled to 5°–10° C., neutralized with 1.5 ml of 37% HCl and the separated oil is triturated until solidification. Upon filtration and recrystallization from water, the product is obtained in a 73.2% yield;

m.p. 192°–193° C.

For $C_9H_{12}N_2O_3S_2$ Calc. C %=41.52 H %=4.68 N %=10.76 S %=24.68 Found C %=41.10 H %=4.64 N %=10.65 S %=24.47

$[\alpha]_D^{20} = -130.65°$ (C=1 in MeOH)

$^1$H NMR (DMSO/TMS) δ=1.8–2.6 (m, 4H, C$\underline{H_2}$C$\underline{H_2}$); 3.1–3.4 (m, 2H, SC$\underline{H_2}$C); 4.15–4.7 (s, 2H, N—C$\underline{H_2}$S); 4.8–5.1 (m, 2H, C$\underline{H}$CO); 10.2 (s, 1H, CO$\underline{OH}$).

EXAMPLE 3

To a stirred solution of 14.5 g (0.1 mole) of 5-thioxo-L-proline (T. P. Andersen et al., Liebigs Ann. Chem., 1986, 269–279) and 16.1 g (0.1 mole) of ethyl L-thiazolidine-4-carboxylate in 400 ml of tetrahydrofuran, cooled to 0° C., 20.6 g of dicyclohexylcarbodiimide are added in small portions. The reaction mixture is stirred for one hour at 0° C. and for 12 hours at room temperature, then it is filtered, the solvent is concentrated under vacuum and the residue is triturated with ethyl ether to give 21 g (72.9%) of the product with the same characteristics of that obtained in Example 1.

We claim:

1. Compounds of general formula (I)

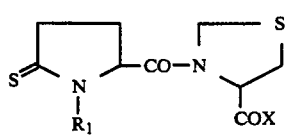

wherein $R_1$ is hydrogen, $C_1$–$C_8$ alkyl, $C_6$–$C_8$ aryl and aralkyl, $C_2$–$C_{10}$ acyl, $C_2$–$C_{10}$ straight or branched alkoxyalkyl containing 1–3 oxygen atoms, $C_3$–$C_8$ alkylcarbonylalkyl, and X is —OH, $C_1$–$C_4$ alkoxy, aralkoxy and to the pharmaceutically acceptable salts thereof.

2. 3-L-(5-thioxo-L-propyl)thiazolidine-4-carboxylic acid.

3. A compound according to claim 1 wherein $R_1$ is hydrogen, $C_{1-4}$ alkyl, phenyl, benzyl, acetyl, methoxyethyl, methoxy- or ethoxy-carbonyl-methyl or -ethyl; and X is hydroxy, methoxy, or ethoxy.

4. A pharmaceutical composition having immunostimulating, antitoxic, antiradical and antiageing activities comprising as the principal active ingredient an effective amount of a compound according to claim 1 in admixture with a pharmaceutically acceptable carrier.

5. A pharmaceutical composition according to claim 4 in which the compound is 3-L-(5-thioxo-L-prolyl)-thiazolidine-4-carboxylic acid.

6. A process for treating a patient suffering from any of immunodeficiency, autoimmuno disease, ageing and broncho-pulmonary disease which comprising administering to said patient a composition according to claim 4.

* * * * *